(12) United States Patent
Hengstenberg et al.

(10) Patent No.: US 7,758,735 B2
(45) Date of Patent: Jul. 20, 2010

(54) OPEN ELECTROCHEMICAL SENSOR

(75) Inventors: Andreas Hengstenberg, Reinfeld (DE); Peter Tschuncky, Lübeck (DE)

(73) Assignee: Drägerwerk Aktiengesellschaft, Lübeck (DE)

( * ) Notice: Subject to any disclaimer, the term of this patent is extended or adjusted under 35 U.S.C. 154(b) by 767 days.

(21) Appl. No.: 11/279,316

(22) Filed: Apr. 11, 2006

(65) Prior Publication Data
US 2006/0249382 A1 Nov. 9, 2006

(30) Foreign Application Priority Data
May 4, 2005 (DE) .................. 10 2005 020 719

(51) Int. Cl.
*G01N 27/26* (2006.01)
(52) U.S. Cl. .................. 204/412; 204/409; 204/431; 204/432; 204/435
(58) Field of Classification Search ......... 204/400–435, 204/193; 205/775–794.5
See application file for complete search history.

(56) References Cited

U.S. PATENT DOCUMENTS

| | | | | |
|---|---|---|---|---|
| 4,587,003 A | * | 5/1986 | Tantram et al. | 204/412 |
| 5,858,574 A | * | 1/1999 | Grignol | 429/210 |
| 6,488,836 B1 | * | 12/2002 | Nakata et al. | 205/784 |
| 6,559,005 B2 | * | 5/2003 | Gutsche et al. | 438/255 |
| 6,686,090 B2 | * | 2/2004 | Inagaki et al. | 429/218.1 |
| 2002/0134677 A1 | * | 9/2002 | Peng | 204/402 |
| 2004/0033414 A1 | * | 2/2004 | Rohrl | 429/46 |

FOREIGN PATENT DOCUMENTS

| | | |
|---|---|---|
| DE | 10245337 A1 | 4/2004 |
| GB | 1552620 | 9/1979 |
| GB | 2332528 A * | 6/1999 |
| GB | 2 395 564 | 5/2004 |
| JP | 2003172722 | 6/2003 |
| JP | 2003172723 A | 6/2003 |
| JP | 2004333163 | 11/2004 |
| WO | WO2004/017443 | 2/2004 |

OTHER PUBLICATIONS

Kaneko et. al, Properties of Ion Gels Obtained by in situ Polymerization of Vinyl Monomers in Ionic Liquids, 2001, Extended Abstracts. Symposium on Solid State Ionics in Japan, vol. 27, p. 200-201 (2001).*
Hodgson et al.; Electrochemical Sensor for the Detection of SO2 in the Low-ppb Range; Anal. Chem. 1999, 71, 2831-2837.
Weber et al.; Elektrochemische Sensoren zur Detektion von Toxischen Gasen; Industrielle Gassensorik, Sensorik; Band 11 (2001).
Hamann et al.; Elektrochemie, Auflage 2005 and Auflage 1998.
Kitzelmann et al.; Elektrochemische Gassensoren, Wirkungsweisen und Moeglichkeiten zur Funktionsueberwachung; Technisches Messen 62 (1995).

* cited by examiner

*Primary Examiner*—Nam X Nguyen
*Assistant Examiner*—Jennifer Dieterle
(74) *Attorney, Agent, or Firm*—McGlew and Tuttle, P.C.

(57) ABSTRACT

An electrochemical sensor with at least one ionic liquid (4) as the electrolyte, contains at least one electrode (1), whose active surface is substantially larger than the geometric area covered by said electrode (1). The electrolyte and at least one of the electrodes (1, 2, 3) are in direct contact with the ambient atmosphere.

20 Claims, 5 Drawing Sheets

OPEN ELECTROCHEMICAL SENSOR

CROSS REFERENCE TO RELATED APPLICATIONS

This application claims the benefit of priority under 35 U.S.C. §119 of German Patent Application DE 10 2005 020 719.7 filed May 4, 2005, the entire contents of which are incorporated herein by reference.

FIELD OF THE INVENTION

The present invention pertains to an electrochemical sensor with open lying working electrode and electrolyte reservoir.

BACKGROUND OF THE INVENTION

Electrochemical sensors are used in many different ways to detect chemical components in fluid media, for example, in gases.

Due to their principle of action, electrochemical sensors contain a plurality of electrodes, which communicate with one another via an electrolyte. The most common devices are amperometric sensors and comprise a working electrode and a counterelectrode or a working electrode and a counterelectrode, which is complemented by a reference electrode. The working electrode is also occasionally called a measuring electrode, and the counterelectrode is occasionally called an auxiliary electrode.

These electrochemical sensors normally comprise, a large number of individual components, which are arranged piece by piece in usually injection-molded plastic housings in a large number of steps. Present are, among other things, the aforementioned electrodes, which are mostly completely surrounded by electrolyte. In this conventional design a relatively large equalizing volume must be provided for wetting all electrodes over the broadest possible range of ambient humidities, taking into account the hygroscopic properties of most electrolytes and preventing the sensor from bursting or drying out. Minimum sizes of conventional sensor designs, which can affect a decision for or against their use, follow from the requirements imposed on the electrolyte volume as well as other design constraints.

Most electrochemical sensors have such a design that the interior space of the sensor is closed against the environment of the sensor. The access of gases or substances to be detected, which is necessary for the desired detection reaction, normally takes place through gas-permeable membranes. These gas-permeable membranes consist mostly of hydrophobic, fine-porous polymers, which retain, for example, an aqueous electrolyte in the interior space of the sensor, but offer a lower resistance to gases entering by diffusion. As an alternative, the diffusion of substances to be detected also takes place by volume diffusion through closed, nonporous polymer films. However, this method is used only for the measurement of substances that occur at a high concentration (e.g., $O_2$ in the atmosphere). The substances to be detected must reach the working electrode in any case. The working electrode is normally arranged directly on the membrane intended for the diffusive entry of the substances to be detected or is arranged at a closely spaced location from same in the electrolyte space.

The principle of diffusion of the substance to be detected through a membrane has a number of drawbacks. Open-pore membranes have a very large surface. If such membranes are used to define the electrolyte space, adsorption phenomena may adversely affect the properties of the sensor. Open-pore and nearly open-pore membranes limit the diffusion in any case, i.e., they limit the access of gas to the working electrode and as a result reduce the sensitivity of an electrochemical sensor. This reduction in sensitivity emerges greatly in case of the use of nonporous membranes.

Moreover sealing of the interior electrolyte space of the sensor may lead to pressure differences against the environment of the sensor and often requires additional design measures for stabilizing the sensor housing. Another drawback is the strong temperature dependence of diffusion processes. If the substance to be detected reaches the working electrode by diffusion through a membrane, the sensitivity of the electrochemical sensor itself becomes temperature-dependent. A complicated temperature compensation may thus become necessary.

Open-pore membranes are, moreover, usually sensitive to rapid changes in pressure because these often lead to penetration of the electrolyte into the pores of the membrane. This is frequently followed by failure of the sensor affected.

If the working electrode is in direct contact with the permeation membrane, it is often difficult to bring about a connection between the working electrode and the membrane that is stable over the long term. However, this is necessary because the diffusion behavior of the substance to be detected is affected by changes in this contact, i.e., through penetrating electrolyte or minimum changes in distance between electrode and membrane. In particular, an electrolyte film forming between the membrane and the working electrode acts as an additional and difficult-to-calculate diffusion barrier.

The sensitivity of electrochemical sensors is determined, in addition, by the size of the effective electrode surface.

It is known that it is possible to abstain from delimiting membranes within electrochemical sensors (GB 1,552,620). As a result, there is a great loss of electrolyte in the device described there. This loss is compensated by a refilling device. However, such a refilling device means increased technical effort. In addition, the signal transduced by such a sensor depends strongly on the degree of wetting of the measuring electrode. Frequent calibrations become necessary as a result.

It is known, furthermore, that ionic liquids can be used as novel electrolyte substances in electrochemical sensors.

Ionic liquids, which are also called molten salts, have acquired increasing significance in electrochemistry in recent years because of their increasing stability to atmospheric conditions (moisture, $O_2$) and are known as an electrolyte or an electrolyte component (DE 10245337 A1, JP2003172723 and US 20040033414 A1). The use of such liquids in membrane-covered or encapsulated electrochemical sensors is described in these documents. As a result, the sensors described have all the drawbacks that are associated with increased resistance to entry of the target gas. However, decreasing maximum allowable workplace concentration values and new measuring tasks do require electrochemical sensors with markedly improved sensitivity.

SUMMARY OF THE INVENTION

The object of the present invention is to provide an electrochemical sensor that avoids as many of the drawbacks of the state of the art as possible. In particular, such a sensor shall have a simple design, small size, long-term stability and the highest possible sensitivity with good reproducibility of the values measured.

The present invention is based on the fact that the sensitivity of sensors can be improved by eliminating membranes, which limit the access of the target gas. Devices for compensating electrolyte losses can be eliminated in an open design if electrolytes are used that have such a low vapor pressure that they do not evaporate to a detectable extent during the typical service life of electrochemical sensors.

In particular, the use of ionic liquids as electrolyte material makes it possible to avoid membranes as sensor-confining elements and thus eliminate the drawbacks of conventional electrochemical sensors which were described in the introduction.

At temperatures at which electrochemical sensors are usually used, ionic liquids have no measurable vapor pressure. It is therefore not necessary to take any measures to compensate losses of electrolyte due to evaporation even if the electrolyte, for example, on an electrolyte support, is in direct contact with the ambient atmosphere over its entire surface.

The low, often undetectable volatility of ionic liquids makes it possible to use electrodes directly exposed to atmosphere in an electrochemical sensor which can be permanently maintained in an electrochemically active state by means of such an electrolyte. Loss of electrolyte and problems with the resupply of electrolyte are eliminated. Permanent electrolytic contacting of the working electrode can be ensured without a separate electrolyte reservoir becoming necessary. It is thus also possible to miniaturize the entire sensor, because electrolyte and compensating volumes to buffer the variations in the quantity of electrolyte which are due to the moisture content are eliminated. The amount of electrolyte needed is drastically reduced compared to all other known electrolytes.

Moreover, electrochemical sensors according to the present invention have electrodes whose active surface is substantially larger than the geometric area covered by the electrodes. This can be embodied by measures taken to enlarge the surface, i.e., microstructuring, by a manufacturing method that leads to porous structures or by selecting porous electrode materials. The sensitivity of the sensors can thus be increased considerably compared to sensors with electrodes without an enlarged surface, which in turn counteracts miniaturization. Even a surface enlarged by a factor of 5 makes it possible to manufacture very small sensitive gas sensors. Substantially greater increases can be achieved by special manufacturing methods. By skillfully setting the process parameters during sputtering processes, it is possible to produce active surfaces, e.g., on porous or rough substrates that are larger than the geometric surface (projection or footprint) of the electrodes by a factor of 50. This factor can be increased even to more than 500 by special printing methods.

In case of the use of electrodes with enlarged surface, the use of conventional electrolytes requires measures that prevent variations in wetting, because these considerably compromise the reproducibility of the measured values. The state of the art was to ensure that the microstructures of the electrodes that may possibly be present were always maintained completely covered by electrolyte bath, mostly by filling in a copious amount of electrolyte. However, the thickness of the electrolyte layer covering the electrodes determines the diffusion of the target gas to the working electrode, and the advantage of the enlarged surface is therefore partially lost in electrolytes "flooded" in this manner. When conventional, for example aqueous electrolytes are used, wetting of the open lying electrodes to a small thickness of electrolyte layer implies the risk that surface areas of the electrodes dry up already in case of small losses due to evaporation, and therefore changes in the measuring characteristics of the sensor affected arise.

Due to the use of ionic liquids, sensors according to the present invention make wetting with very thin electrolyte films possible even when electrodes with extremely enlarged surfaces and fine surface structures are used, without an impairment of the reproducibility of the sensor output. The advantage of the enlarged surface can be optimally utilized if the electrolyte layer on the electrode surface is so thin that it is able to follow the contour of the surface-enlarging microstructures. This is equally true of the surface of pores that may possibly be present, i.e., an inner surface of the electrodes, which can thus also be regarded as an active electrode surface.

It was found that wetting of electrodes with the electrolyte layer that extensively but incompletely covers the electrode surface has an especially advantageous effect on the sensitivity of electrochemical sensors according to the present invention. Three-phase boundaries are thus obviously formed especially effectively between the electrode material, the electrolyte and the target gas. Electrolyte coverages of at least 60% of the electrode surface proved to be optimal for this application.

It is advantageous if at least the working electrode has an enlarged surface compared to its geometric dimensions. However, the other electrodes that are in contact with the electrolyte may also have such an enlarged surface in sensors according to the present invention.

Ionic liquids based on certain classes of cations combined with halide, sulfate, sulfonate, borate, phosphate, antimonate, amide, imide or methanate ions proved to be suitable electrolyte substances. The following classes of cations proved to be advantageous: Monosubstituted imidazolium ions, disubstited imidazolium ions, trisubstituted imidazolium ions, pyridinium ions, pyrrolidinium ions, phosphonium ions, ammonium ions, guanidinium ions and osouronium ions.

Ionic liquids with especially low melting points, for example, ethyl methyl imidazolium bis(trifluoromethylsulfonyl)iride, proved to be especially advantageous for outdoor applications.

It is advantageous if the electrodes consist of Pt, Ir, Au, C, DLC, diamond, Ru or a mixture of at least some of the substances, and the carbon-based materials may also comprise carbon fibers or carbon nanotubes.

The present invention will be explained in greater detail on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
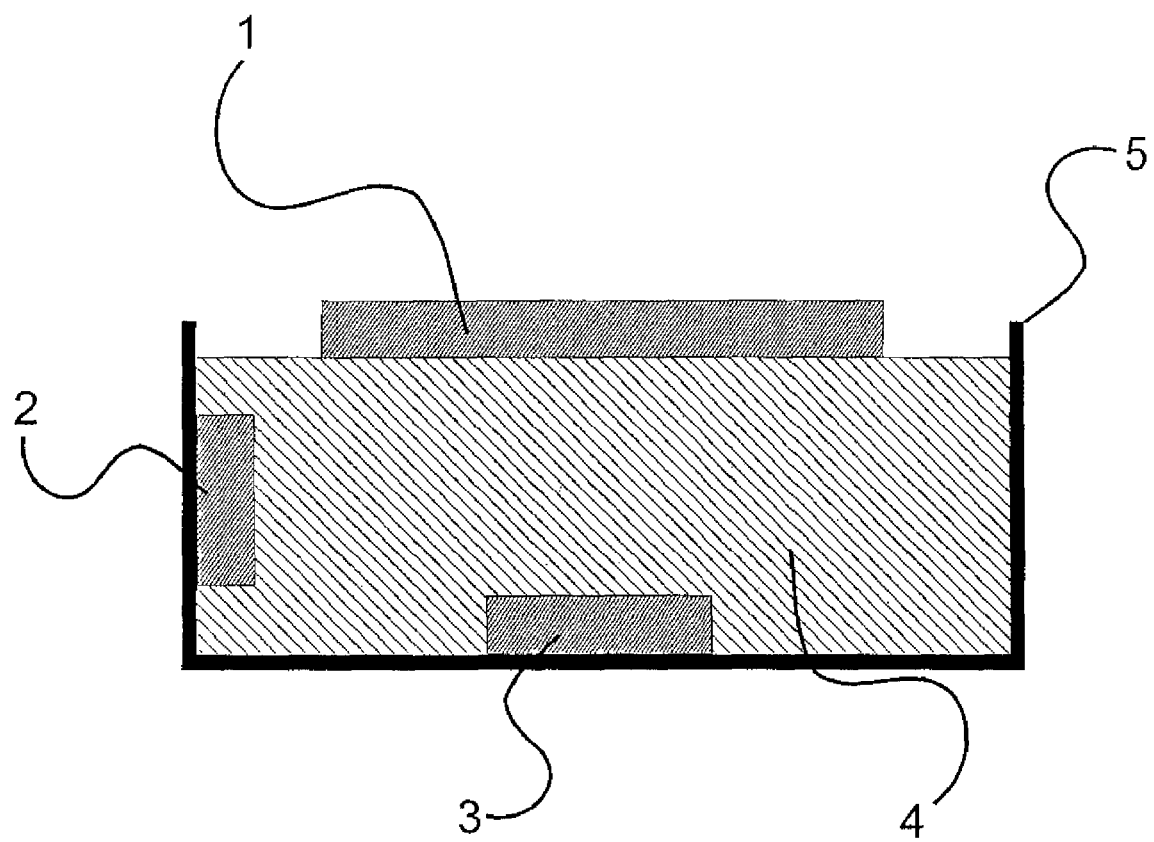
FIG. 1 is a schematic sectional view showing the design of an electrochemical sensor according to the present invention.

Referring to the drawings in particular, FIG. 1 shows the design of an electrochemical sensor according to the present invention. A working electrode 1, a reference electrode 2 and an auxiliary electrode 3 are in contact with the electrolyte, an ionic liquid 4, which is in the stabilized form in the form of a gel from the ionic liquid with a chemically inert, preferably perfluorinated gelling agent, e.g., PVDF (polyvinylidene difluoride). For better fixation, the arrangement is accommodated in a vat-shaped housing 5, which consists of a nonconductive material. Such a design can be manufactured in an especially simple manner. The stabilized ionic liquid offers sufficient strength to be stamped out as a thin disk and to be subsequently provided with electrodes on one side or on both sides. The electrodes are applied by sputtering, sintering or printing. By setting corresponding process parameters, this makes it possible to deposit electrodes that have an enlarged surface according to the present invention. The electrodes are contacted, for example, via wires placed on them.

As an alternative, the bottom and/or the walls of the vat-shaped housing may be provided with electrodes prepared by sputtering, printing, rolling or vapor deposition. The electrodes are then applied with the contacting paths belonging to them. The different processes for applying the electrodes make it in turn possible to manufacture electrodes with enlarged surface according to the present invention.

Figure 2:
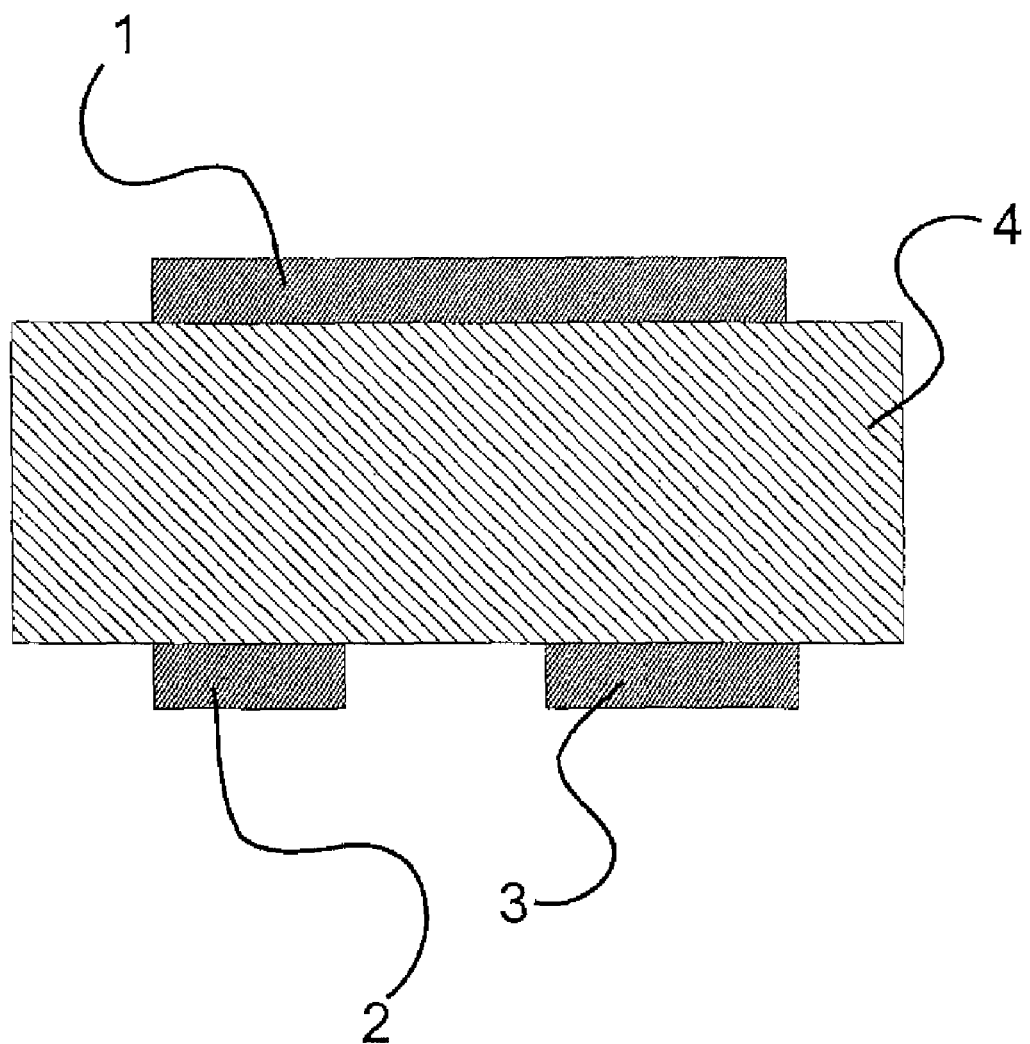
FIG. 2 is a schematic sectional view showing a sensor according to the present invention of a housing-free design.

FIG. 2 shows a sensor according to the present invention of a housing-free design. The ionic liquid 4 is deposited in an open support. This open support is a porous membrane, whose pores are filled with the ionic liquid. Porous electrodes 1, 2, 3, which are wetted by capillary action, are applied by sputtering or printing. As an alternative, the reference electrode 2 and the auxiliary electrode 3 may also be designed as smooth electrodes.

Figure 3:
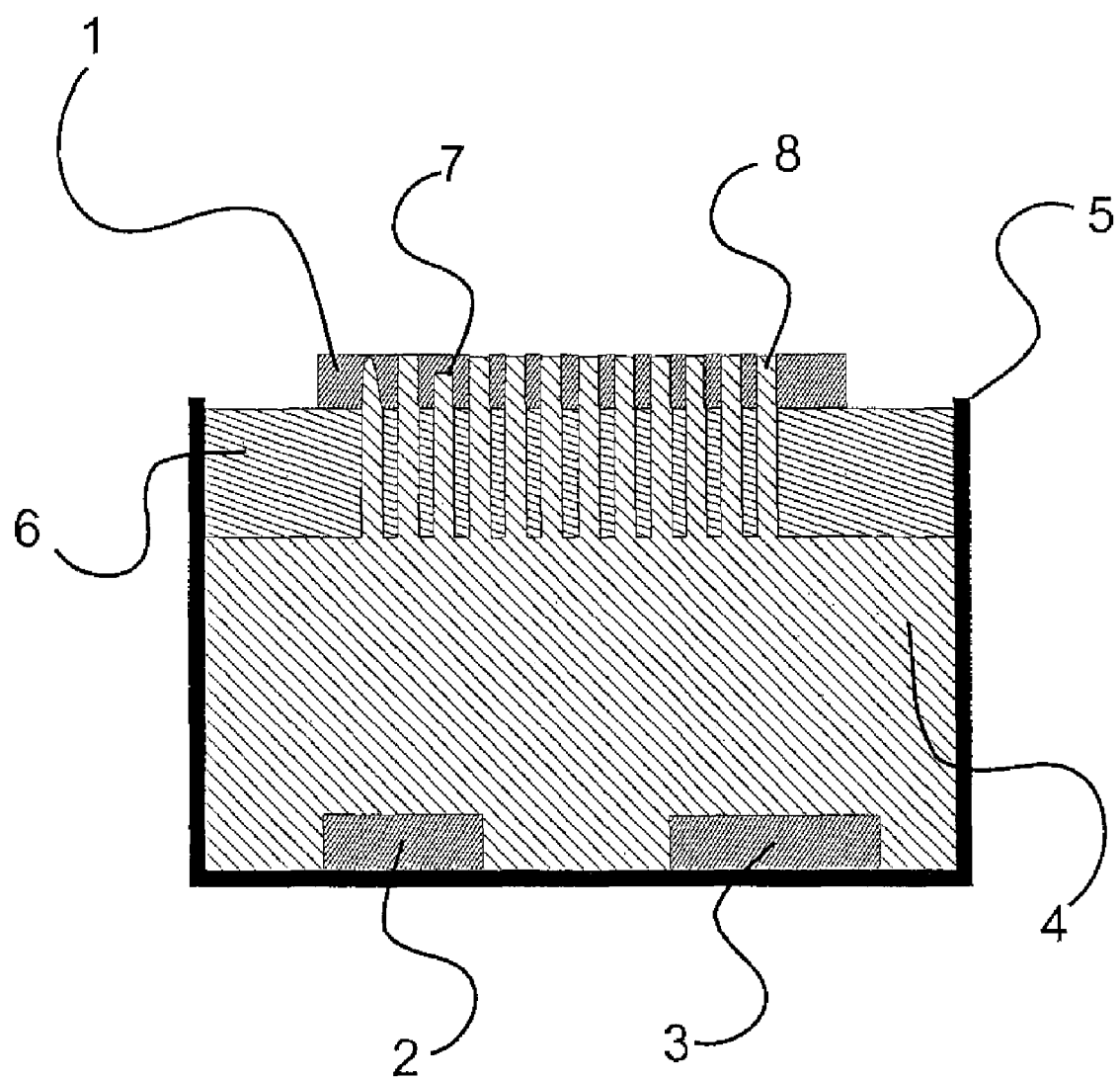
FIG. 3 is a schematic sectional view showing a sensor according to the present invention, whose working electrode was microstructured.

FIG. 3 shows a sensor according to the present invention, whose working electrode was microstructured. The material of the working electrode 1 was applied for this purpose on a planar, electrically nonconductive support 6 made of silicon on one side, and this electrode-substrate combination was subjected to a structuring process. Individual depressions 7 or openings 8 passing completely through the working electrode 1 can be formed by suitably selecting the process parameters of the structuring process. Both types of structuring can be carried out simultaneously or definitely by one of the two alternatives. The structured support 6 is in flat contact with an electrolyte reservoir containing an ionic liquid 4. The openings 8 or depressions 7 in the working electrode fill up with the ionic liquid from the rear side under the effect of capillary forces. As a result, a large-area contact develops between the electrolyte and the electrode. At the same time, the electrolyte is in direct contact with the ambient atmosphere on the outer side of the working electrode 1. Optimal wetting of the electrode surface is set by selecting the size of the holes and the spacing between them.

Figure 4:
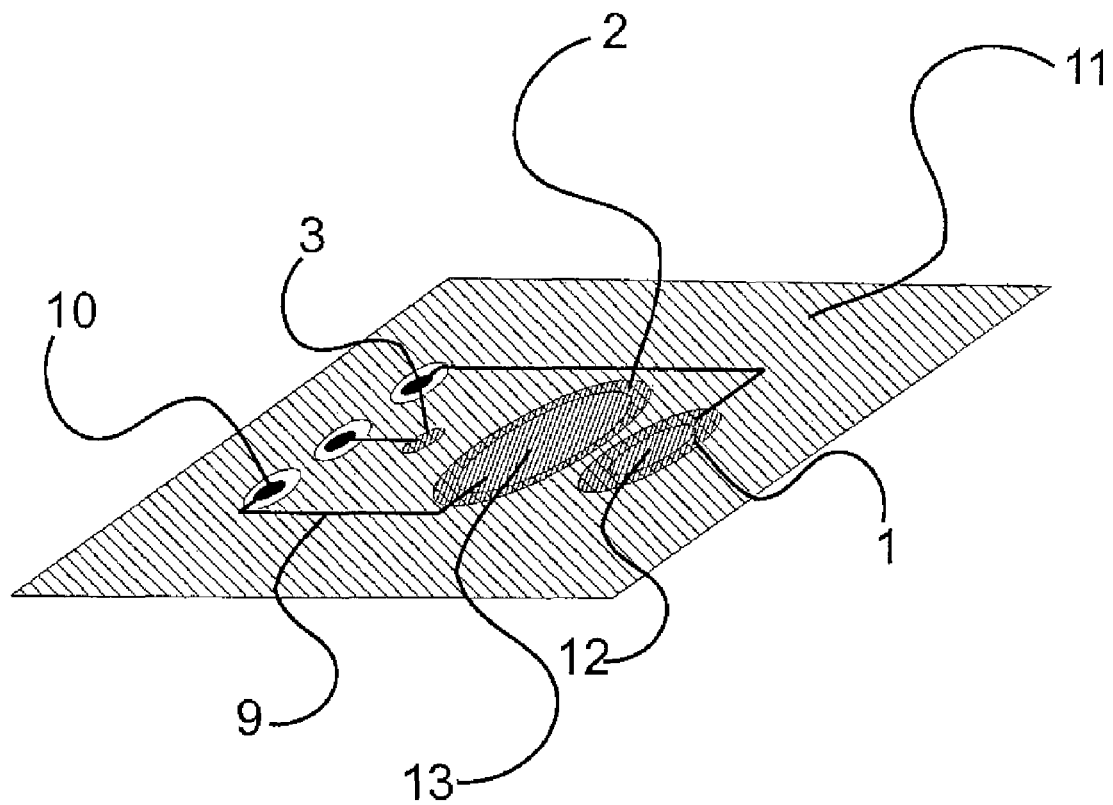
FIG. 4 is a schematic view showing a laminated three-electrode sensor without membrane cover.

FIG. 4 shows a planar three-electrode sensor without membrane cover. The three electrodes 1, 2, 3, which are contacted via feed paths 9 and are connected to contact pads 10, are located in a housing 11 consisting of films welded to one another.

At least the sensor or working electrode 1 is directly in contact with the surrounding atmosphere without any membrane cover via a huge opening 12 stamped into the housing 11 and partial covered by the electrolyte. However, this may also be true for the counter electrode 2 with the opening 13 belonging to it. The electrodes consist of a porous material and are embedded in an electrolyte reservoir. The electrolyte reservoir is filled with ethyl methyl imidazolium bis(trifluoromethylsulfonyl)iride and is enclosed by the housing 11. Via the opening 12 in front of the porous electrode 1, the electrolyte and electrode are likewise in direct contact with the ambient atmosphere.

Figure 5:
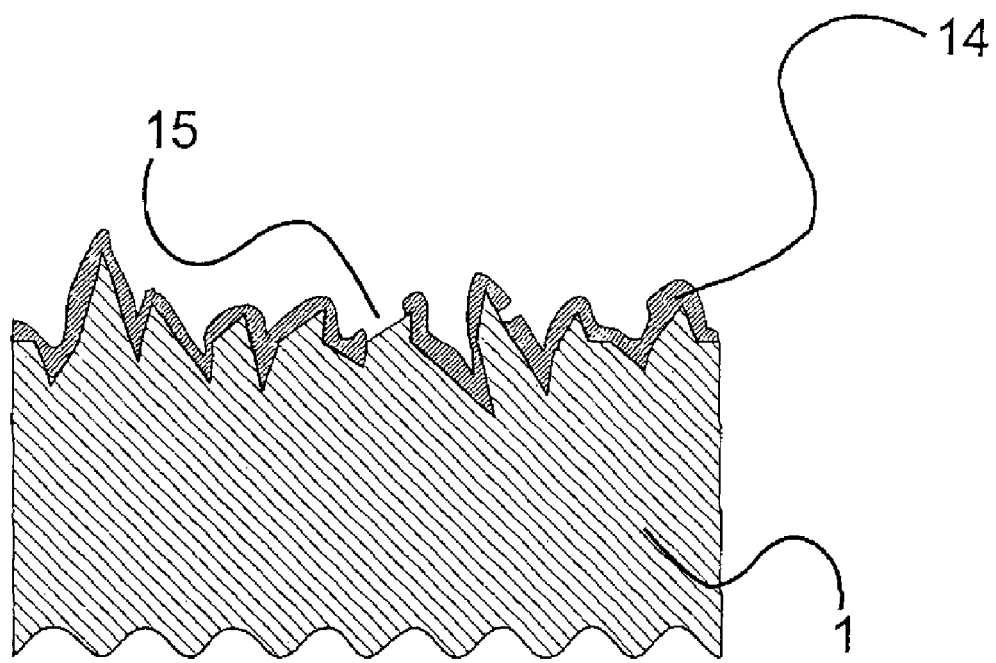
FIG. 5 shows a detail of the surface of a nearly completely electrolyte-covered, structured electrode.

FIG. 5 shows a detail of the surface of a nearly completely electrolyte-covered, structured electrode 1. The surface is covered with an electrolyte layer 14, which is so thin that it follows the contour of the microstructures that enlarge the surface. The surface has small areas 15 in which the coverage is absent. The electrode surface is in direct contact with ambient atmosphere. Due to the use of an ionic liquid as the electrolyte, the overall amount of uncovered areas 15 remains stable in size. This means that there are no variations in the degree of coverage over a longer time. Such a geometry has proved to be especially effective.

While specific embodiments of the invention have been shown and described in detail to illustrate the application of the principles of the invention, it will be understood that the invention may be embodied otherwise without departing from such principles.

What is claimed is:

1. An electrochemical sensor comprising:
    a counterelectrode;
    a reservoir of an ionic liquid as an electrolyte, said reservoir comprising a surface containing said electrolyte;
    a working electrode having an active surface, said active surface having an active surface area, said working electrode having a geometric area, said active surface area being substantially larger than said geometric area, said working electrode and said surface containing said electrolyte being in direct contact with ambient atmosphere, said electrolyte covering and being in contact with at least a portion of said active surface of said working electrode, whereby said at least said portion of said active surface of said working electrode is in contact with said reservoir; and
    a reference electrode and an additional electrode, said working electrode with said active surface being covered by an electrolyte layer comprised of said ionic liquid with said electrolyte incompletely covering said active surface of said working electrode.

2. An electrochemical sensor in accordance with claim 1, wherein said active surface is larger, at least by a factor of 5, than said geometric area.

3. An electrochemical sensor in accordance with claim 1, wherein said active surface is larger, at least by a factor of 50, than said geometric area.

4. An electrochemical sensor in accordance with claim 1, wherein said active surface is larger, at least by a factor of 500, than said geometric area.

5. An electrochemical sensor in accordance with claim 1, wherein said working electrode with said active surface comprises a microstructured surface.

6. An electrochemical sensor in accordance with claim 1, wherein said working electrode with said active surface consists of a porous material.

7. An electrochemical sensor in accordance with claim 1, wherein said additional electrode has an additional electrode active surface and an additional electrode geometric area, said electrolyte engaging at least a portion of said additional electrode active surface and at least a portion of said additional electrode geometric area.

8. An electrochemical sensor in accordance with claim 1, wherein said working electrode with said active surface comprises a microstructured surface wherein at least said active surface is covered by an electrolyte layer comprised of said ionic liquid, said electrolyte layer being thin enough that said electrolyte layer follows a contour of microstructures of said microstructured surface.

9. An electrochemical sensor in accordance with claim 1, wherein said working electrode is covered by an electrolyte layer comprised of said ionic liquid with said electrolyte covering at least 60% of said active surface.

10. An electrochemical sensor in accordance with claim 1, wherein said electrolyte comprises an ionic liquid which contains a cation from one of the following classes: monosubstituted imidazolium ions, disubstituted imidazolium ions, trisubstituted imidazolium ions, pyridinium ions, pyrrolidinium ions, phosphonium ions, ammonium ions, guanidinium ions and osouronium ions.

11. An electrochemical sensor in accordance with claim 1, wherein said electrolyte comprises an ionic liquid, which contains as the anion halide, sulfate, sulfonate, borate, phosphate, antimonate, amide, imide or methanate ions.

12. An electrochemical sensor in accordance with claim 1, wherein said electrolyte comprises ethyl methyl imidazolium bis(trifluoromethylsulfonyl)imide.

13. An electrochemical sensor in accordance with claim 1, wherein PVDF is contained for stabilizing the electrolyte.

14. An electrochemical sensor in accordance with claim 1, further comprising a perfluorinated gelling agent for stabilizing said electrolyte.

15. An electrochemical sensor in accordance with claim 1, wherein said electrodes are made of at least one of the materials from the group of Pt, Ir, Au, C, DLC, diamond and Ru, wherein carbon-based materials of the group also comprise carbon fibers or carbon nanotubes.

16. An electrochemical sensor in accordance with claim 7, wherein said active surface of said working electrode and said additional electrode active surface combined are larger than the geometric area covered by said working electrode and said additional electrode.

17. An electrochemical sensor comprising:
a structure comprising a reservoir of an ionic liquid as a liquid electrolyte, said liquid electrolyte defining a liquid gas interface of said reservoir;
a reference electrode;
a counter electrode; and
a working electrode having an active surface area and a geometric area, said geometric area comprising a distance from one edge of said working electrode to another edge of said working electrode, said active surface area being of a dimension that is substantially greater than a dimension of said geometric area, said electrolyte covering and being in contact with at least a portion of said active surface of said working electrode such that said active surface is only partially covered by said electrolyte, said structure defining an open side, wherein no portion of said structure extends along said open side, said open side being exposed to an ambient atmosphere, said electrolyte and said working electrode being exposed to the ambient atmosphere at said open side of said structure so as to have said liquid gas interface of said reservoir and a surface of said working electrode in direct contact with the ambient atmosphere, wherein said reservoir and said working electrode are not covered by said structure and no structure of the electrochemical sensor is disposed between the ambient atmosphere, said liquid gas interface and said working electrode, said electrolyte being located opposite said active surface of said working electrode.

18. An electrochemical sensor in accordance with claim 17, wherein said working electrode having said active surface comprises a microstructured surface.

19. An electrochemical sensor in accordance with claim 17, wherein said working electrode having said active surface consists of a porous material.

20. An electrochemical sensor comprising:
a reservoir of an ionic liquid as an electrolyte;
a reference electrode;
a counter electrode;
a working electrode having an active surface area and a geometric area comprising a distance from one edge of said working electrode to another edge of said working electrode, said active surface area being of a dimension that is substantially greater than a dimension of said geometric area, said electrolyte extending along at least a portion of said active surface area such that said electrolyte does not completely cover said active surface area, said electrolyte being located opposite said active surface area of said working electrode, said reservoir having an ambient atmosphere contacting surface, said ambient atmosphere contacting surface comprising said electrolyte, said working electrode having a working electrode surface, said ambient atmosphere contacting surface and said working electrode surface being exposed to an ambient atmosphere so as to be in direct contact with the ambient atmosphere, said ambient atmosphere contacting surface and said working electrode being located at a spaced location from a position in said ambient atmosphere, wherein no structure of the electrochemical sensor is arranged between said position in said ambient atmosphere and said surface containing said electrolyte and said working electrode.

\* \* \* \* \*